(12) United States Patent
Bregulla (10) Patent No.: US 8,002,818 B2
(45) Date of Patent: Aug. 23, 2011

(54) MODULAR VASCULAR PROSTHESIS HAVING AXIALLY VARIABLE PROPERTIES AND IMPROVED FLEXIBILITY AND METHODS OF USE

(75) Inventor: Rainer Bregulla, Balingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 320 days.

(21) Appl. No.: 11/067,090

(22) Filed: Feb. 25, 2005

(65) Prior Publication Data

US 2006/0195175 A1    Aug. 31, 2006

(51) Int. Cl.
*A61F 2/82* (2006.01)
(52) U.S. Cl. .................................................. 623/1.16
(58) Field of Classification Search ............... 623/1.15, 623/1.16, 1.42, 1.13
See application file for complete search history.

(56) References Cited

U.S. PATENT DOCUMENTS

| | | | |
|---|---|---|---|
| 4,580,568 A | 4/1986 | Gianturco | |
| 4,739,762 A | 4/1988 | Palmaz | |
| 5,632,771 A | 5/1997 | Boatman et al. | |
| 5,741,327 A * | 4/1998 | Frantzen | 623/1.34 |
| 5,824,037 A | 10/1998 | Fogarty et al. | |
| 5,824,046 A * | 10/1998 | Smith et al. | 623/1.13 |
| 6,015,815 A | 1/2000 | Mollison | |
| 6,048,361 A * | 4/2000 | Von Oepen | 623/1.11 |
| 6,129,755 A | 10/2000 | Mathis et al. | |
| 6,187,036 B1 * | 2/2001 | Shaolian et al. | 623/1.15 |
| 6,231,598 B1 | 5/2001 | Berry et al. | |
| 6,293,966 B1 | 9/2001 | Frantzen | |
| 6,336,937 B1 | 1/2002 | Vonesh et al. | |
| 6,409,754 B1 * | 6/2002 | Smith et al. | 623/1.16 |
| 6,503,271 B2 | 1/2003 | Duerig et al. | |
| 6,540,777 B2 | 4/2003 | Stenzel | |
| 6,562,067 B2 | 5/2003 | Mathis | |
| 6,585,764 B2 | 7/2003 | Wright et al. | |
| 6,599,314 B2 | 7/2003 | Mathis | |
| 6,814,746 B2 * | 11/2004 | Thompson et al. | 623/1.11 |
| 6,945,995 B2 | 9/2005 | Nicholas | |
| 7,235,093 B2 | 6/2007 | Gregorich | |
| 2001/0027340 A1 * | 10/2001 | Wright et al. | 623/1.15 |
| 2001/0053929 A1 | 12/2001 | Vonesh et al. | |
| 2002/0010507 A1 * | 1/2002 | Ehr et al. | 623/1.16 |
| 2002/0111671 A1 | 8/2002 | Stenzel | |
| 2002/0120327 A1 * | 8/2002 | Cox et al. | 623/1.16 |
| 2002/0188343 A1 | 12/2002 | Mathis | |
| 2002/0188347 A1 | 12/2002 | Mathis | |
| 2003/0135265 A1 | 7/2003 | Stinson | |

(Continued)

FOREIGN PATENT DOCUMENTS

DE    203 08 672    9/2003

(Continued)

OTHER PUBLICATIONS

U.S. Appl. No. 11/962,463, filed Jan. 22, 2010, Office Action
U.S. Appl. No. 11/962,463, filed Jun. 25, 2010, Office Action.
U.S. Appl. No. 11/962,463, filed Jan. 21, 2011, Office Action.

*Primary Examiner* — Ryan J Severson
(74) *Attorney, Agent, or Firm* — Workman Nydegger (57) ABSTRACT

The present invention provides a vascular prosthesis featuring a plurality of modular segments interengaged by flexible, and preferably lockable, inter-engageable elements forming joints. The segments may have a number of different mechanical properties and may be assembled by the clinician to customize the prosthesis for a specific patient or application.

30 Claims, 5 Drawing Sheets

U.S. PATENT DOCUMENTS

| | | |
|---|---|---|
| 2003/0135266 A1 | 7/2003 | Chew et al. |
| 2004/0044398 A1 | 3/2004 | Nicholas |
| 2004/0093077 A1* | 5/2004 | White et al. ............ 623/1.16 |
| 2004/0236406 A1* | 11/2004 | Gregorich ............... 623/1.16 |
| 2005/0182475 A1 | 8/2005 | Jen et al. |
| 2006/0030932 A1* | 2/2006 | Kantor et al. ............ 623/1.16 |
| 2006/0069424 A1* | 3/2006 | Acosta et al. ............ 623/1.12 |
| 2009/0005848 A1 | 1/2009 | Strauss et al. |

FOREIGN PATENT DOCUMENTS

| | | |
|---|---|---|
| WO | WO 00/15151 A * | 3/2000 |
| WO | WO 03/049640 | 6/2003 |
| WO | WO 03/075797 A | 9/2003 |
| WO | WO 2004/014256 | 2/2004 |
| WO | WO 2006/089739 | 8/2006 |

* cited by examiner

MODULAR VASCULAR PROSTHESIS HAVING AXIALLY VARIABLE PROPERTIES AND IMPROVED FLEXIBILITY AND METHODS OF USE

FIELD OF THE INVENTION

The present invention relates to vascular prostheses, such as stents, having improved flexibility. More particularly, the present invention relates to stents having modular construction that permit the properties and length of the stent to be customized for a specific patient.

BACKGROUND OF THE INVENTION

Numerous stent designs are known in the art, of which self-expanding and balloon-expandable stents are the predominant commercially available types. Self-expanding stents, such as described in Gianturco U.S. Pat. No. 4,580,568, generally provide good crush-resistance and axially flexibility, thus permitting delivery through tortuous anatomy, but provide lower radial strength once deployed. Balloon-expandable stents, such as typified by Palmaz U.S. Pat. No. 4,739,762, provide high radial strength, but tend to have increased axial rigidity that affects deliverability through tortuous vessels. It has therefore been a goal of many balloon expandable stent designs to enhance axial flexibility of the stent to improve deliverability, and thus the number of potential applications for the device.

Previously known stents generally are provided in a variety of lengths and diameters, so the clinician can select the stent most appropriate for a specific patient. Such stents typically have homogeneous properties along the length of the stent, and provide limited options for customization responsive to the needs of a particular patient.

There may be applications, however, where the best solution for a particular patient would involve a combination of the features of both balloon-expandable and self-expanding stents. It would therefore be desirable to provide a modular stent that permits the clinician to "mix and match" stent modules to build a stent having specific characteristics tailored for a specific patient or application.

For example, it may be desirable to provide a stent having axial modules of variable rigidity and crush-resistance, such as for use in the carotid arteries. Due to the generally exposed nature of these arteries in the region of the neck, situations have been reported where balloon-expandable stents have been subjected to partial crushing. On the other hand, self-expanding stents are susceptible to migration. It therefore may be desirable in certain applications to provide a stent having a resilient central portion and balloon-expandable end regions that permit the stent to be anchored in position.

The ability to vary the mechanical properties of the stent also would permit a stent to include non-metallic components, such as biodegradable or bioabsorbable segments. This ability might prove particularly advantageous where it is desired to deliver a predetermined dose of drug to via drug-eluting segments, for example, by incorporating a specified number of drug-eluting segments into the prosthesis.

As yet another example, U.S. Pat. No. 6,048,361 to Von Oepen describes a stent designed for use in bifurcated vessels having a side branch aperture. As described in that patent, the stent is manufactured with fixed length regions proximal and distal to the aperture. Thus, the stent may not be suitable in some patients because the fixed length of the proximal or distal region may interfere with collateral vessels upstream or downstream of the bifurcation. Accordingly it would be desirable to provide a vascular prosthesis that includes a side branch aperture, but which has proximal and distal regions that may be tailored for a specific patient.

U.S. Pat. No. 5,824,037 to Fogarty et al. describes a modular intraluminal prosthesis, such as for a stent-graft, comprising a plurality of modules having standard interface ends for engaging adjacent modules. The modules employed in the prosthesis may include variations in axial length, cross-section, perimeter, resilient expansive force and axial flexibility. The modules are "locked" together using stitching in combination with the liner material.

One drawback of the prosthesis described in the Fogarty et al. patent is that the prosthesis may lack structural rigidity in the expanded configuration. In particular, the patent describes no mechanism to positively engage the modules other than the liner material. It therefore would be desirable to provide a modular stent wherein the modules cannot be locked together without stitching or a liner material.

The foregoing patent also does not suggest that a modular stent may be used to improve conformance of the stent to a patient's vasculature when used in a bifurcated region, or the desirability of intermixing segments comprising different materials, including bioabsorbable or drug-eluting segments.

It therefore would be desirable to provide a vascular prosthesis comprising a plurality of modular segments interconnected by lockable joints that enhance articulation between adjacent segments during delivery of the prosthesis and enhance structural rigidity of the prosthesis in the deployed configuration.

It also would be desirable to provide a vascular prosthesis comprising a plurality of modular segments interconnected by a plurality of joints wherein the modular segments comprise different materials or strut configurations, thereby permitting the structural rigidity of the vascular prosthesis in the deployed configuration to be tailored for a specific patient or application.

It further would be desirable to provide a vascular prosthesis comprising a plurality of modular segments, wherein one or more segments may be bioabsorbable or drug-eluting, to provide predetermined doses of drug to the vessel wall or intravascularly to a desired tissue region.

It still further would be desirable to provide a vascular prosthesis comprising a plurality of modular segments, wherein one or more segments may be intermixed to provide a desired feature having proximal and distal regions of customizable length, for example for treatment of bifurcated vessels or aneurysms

SUMMARY OF THE INVENTION

In view of the foregoing, it is an object of the present invention to provide a vascular prosthesis comprising a plurality of modular segments interconnected by a plurality of inter-engageable elements that form joints which enhance articulation between adjacent segments during delivery of the prosthesis and enhance structural rigidity of the prosthesis in the deployed configuration.

It is also an object of this invention to provide a vascular prosthesis comprising a plurality of modular segments interconnected by joints wherein the modular segments comprise different materials or strut configurations, thereby permitting the structural rigidity of the vascular prosthesis in the deployed configuration to be tailored for a specific patient or application.

It is another object of the present invention to provide a vascular prosthesis comprising a plurality of modular segments, wherein one or more segments may be bioabsorbable or drug-eluting, to provide predetermined doses of drug to the vessel wall or intravascularly to a desired tissue region.

It is a further object of this invention to provide a vascular prosthesis comprising a plurality of modular segments, wherein one or more segments may be intermixed to provide a desired feature having proximal and distal regions of customizable length, for example for treatment of bifurcated vessels or aneurysms.

These and other objects of the present invention are accomplished by providing a vascular prosthesis having a delivery configuration and an expanded configuration, the prosthesis comprising a plurality of modular segments interengaged by flexible, and preferably lockable, inter-engageable elements that form joints. In accordance with the principles of the present invention, the segments may have a number of different characteristics and may be assembled by the clinician to customize the prosthesis for a specific patient or application.

For example, segments may have differing mechanical properties, such as being self-expanding, balloon-expandable, include differing strut configurations or comprise different materials, such as metal alloys or bioabsorbable or drug-eluting polymers. In addition, individual segments may include specific features, such as a side-branch aperture for bifurcated vessels or a covering for excluding an aneurysm.

In one embodiment, the inter-engageable element used to join the modular segments comprise ball and socket joints that facilitate articulation between adjacent segments during delivery of the stent through tortuous anatomy. Each segment includes proximal and distal ends, wherein each end comprises a plurality of ball elements, socket elements or a combination of ball and socket elements, depending upon the mechanical properties, strut configuration and intended purpose of a given segment. For example, where a segment comprises a hoop having a plurality of generally zig-zag struts, the ball and socket elements may be formed on extensions of the struts of adjacent segments.

In an alternative embodiment, the inter-engageable elements used to join the modular segments comprise intertwined spiral elements that facilitate articulation between adjacent segments during delivery of the stent through tortuous anatomy. Each segment includes proximal and distal ends, wherein each end comprises a spiral element that interengages a spiral element of an adjacent segment. The spiral elements have a common orientation, either clockwise or counterclockwise, depending upon the mechanical properties, strut configuration and intended purpose of a given segment. Each segment illustratively may comprise a hoop having a plurality of generally zig-zag struts, wherein the spiral elements extend may be formed on extensions of the struts of at regular intervals.

In accordance with a preferred aspect of the present invention, interconnected joints are configured to lock when the prosthesis is transitioned from the delivery configuration to the deployed configuration. For example, the socket elements may comprise a pliers-like element that closes to grip the ball elements when the segment is deployed, thereby preventing adjacent segments from disengaging in the deployed configuration. In the alternative embodiment, the interference of the interconnected spiral elements may increase, thereby locking the spiral elements together.

In alternative embodiments of the prosthesis of the present invention, axial flexibility of the prosthesis may be further enhanced by incorporating flexible, physical connections between the struts contained within a given segment Delivery systems for delivering the inventive prostheses of the present invention also are provided.

BRIEF DESCRIPTION OF THE DRAWINGS

The foregoing and other objects of the invention will be apparent upon consideration of the following detailed description, taken in conjunction with the accompanying drawings, in which like reference characters refer to like parts throughout, and in which.

DETAILED DESCRIPTION OF THE INVENTION

Figure 1:
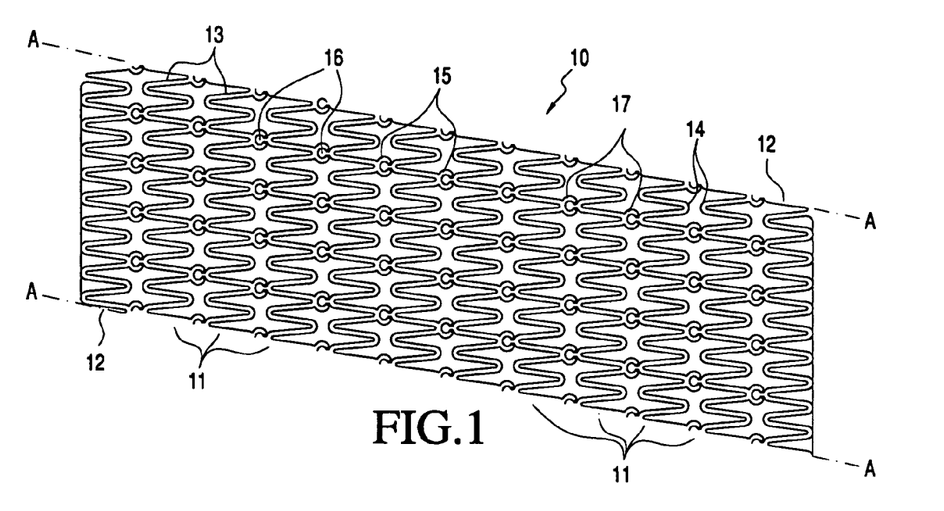
FIG. 1 is a plan view of an exemplary modular vascular prosthesis constructed in accordance with the principles of the present invention that has been cut along line A-A and flattened.

Referring to FIG. 1, a first family of embodiments of a vascular prosthesis of the present invention is described. Vascular prosthesis 10, for example, a stent, is shown cut along line A-A along its longitudinal axis and flattened into a plane for illustrative purposes. Vascular prosthesis 10 comprises a tube-like structure made up of a plurality of interconnected modular segments, including inner segments 11 and end segments 12. In the illustrated embodiment, segments 11 and 12 comprise a plurality of struts 13 joined at the ends by bends 14 to form a generally zig-zag configuration in the deployed configuration. As would be understood by one of ordinary skill in the art, segments 11 and 12 may comprise many alternative strut configurations without departing from the scope of the present invention.

In accordance with the principles of the present invention, joints 15 interconnect segments 11 and 12. In a first preferred embodiment, each joint 15 comprises ball element 16 engaged within socket element 17. Inner segments 11 include ball elements 16 and socket elements 17 at either end, while end segments 12 include such elements on only one end. Ball elements 16 and socket elements 17 preferably are formed as extensions on selected bends 14 disposed between struts 13 around the circumference of the stent.

In FIG. 1, ball elements 16 are disposed on one end of each inner segment 11 while socket elements 17 are disposed on the other end of the segment. Adjacent ball or socket elements are depicted as having one intervening bend 14 around the circumference of the stent, but may include two or more intervening bends. Joints 15 permit a significant degree of articulation between adjacent segments, particularly in the delivery configuration, making the stent highly flexible and thus able to negotiate tortuous anatomy. Although ball elements illustratively are shown as substantially circular structures, ball elements 16 and the corresponding sockets may have other suitable shapes, such as ovals, polygons or diamonds.

The zig-zag configuration of struts 13 and bends 14 depicted in FIG. 1 preferably is formed by laser cutting a solid tube. Vascular prosthesis 10 preferably is flexible enough to conform to the shape of a delicate vessel without substantially remodeling the vessel. In particular, the zig-zag configuration of segments 11 and 12 is expected to conform to a natural curvature of a vessel wall. Of course, other patterns of struts and bends, such as are known in the art, advantageously be used within segments 11 and 12.

Figure 2A:
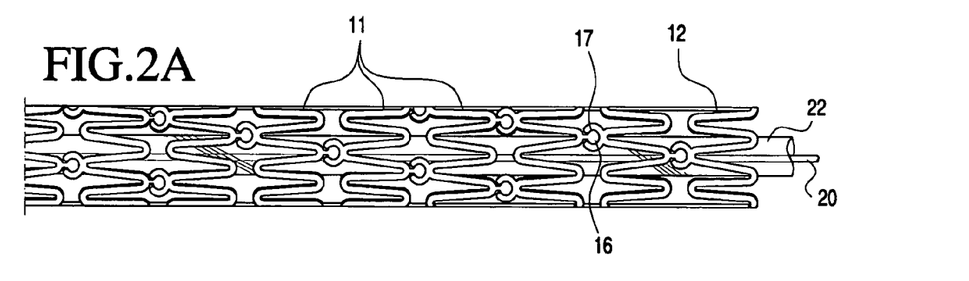
FIGS. 2A and 2B are, respectively, perspective views of the modular vascular prosthesis of FIG. 1 disposed in the delivery configuration around a balloon catheter and in the deployed configuration.

Referring to FIG. 2A, vascular prosthesis 10 comprises a balloon expandable material and is shown crimped in a contracted delivery configuration over balloon 20 of balloon catheter 22. This may be accomplished by assembling a desired number of inner segments 11 between end segments 12 to provide a stent of a desired length, and the assembled stent may then be crimped onto balloon 20 using any of a number of previously-known crimping devices. Because the stent is retained centered on balloon 20, ball elements 16 and socket elements 17 remain in engagement to form a substantially smooth exterior surface of the stent.

Balloon catheter 22 is delivered transluminally to a target site within a patient's vessel using, for example, well-known percutaneous techniques. Vascular prosthesis 10 or portions of catheter 22 may be radiopaque to facilitate positioning within the vessel. The target site may, for example, comprise a stenosed region of the vessel at which an angioplasty procedure has been conducted. In accordance with the present invention, joints 15 permit vascular prosthesis 10 to flex along its length to negotiate tortuous anatomy.

Figure 2B:
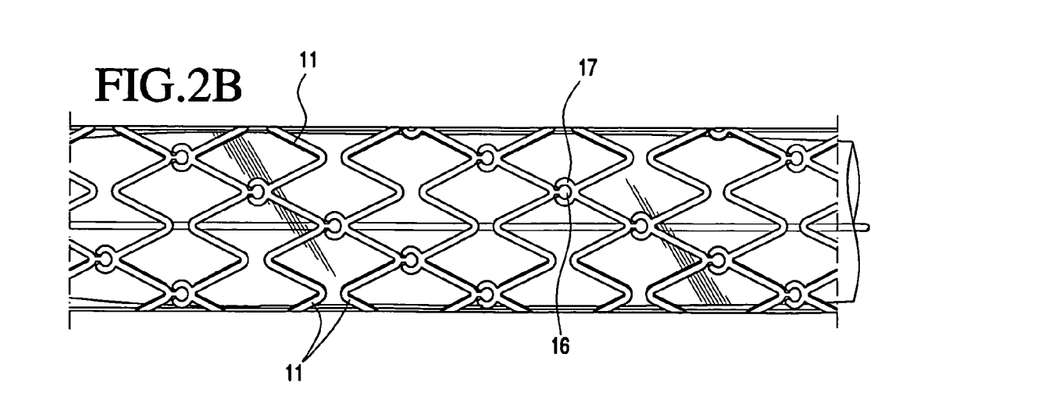

Referring to FIG. 2B, balloon 20 is inflated to expand vascular prosthesis 10 to the deployed configuration in which it engages and supports the wall of the vessel at the target site. As shown in FIG. 2B, ball elements 16 continue to be retained in the socket elements 17 when segments 11 and 12 are radially expanded. Balloon 20 is then deflated and balloon catheter 22 is removed from the vessel, leaving vascular prosthesis 10 supporting the vessel. The web structure of vascular prosthesis 10 provides sufficient radial stiffness to maintain vascular prosthesis 10 in the expanded configuration, with minimal recoil. Vascular prosthesis 10 optionally may comprise an external coating configured to inhibit restenosis.

Figure 3:
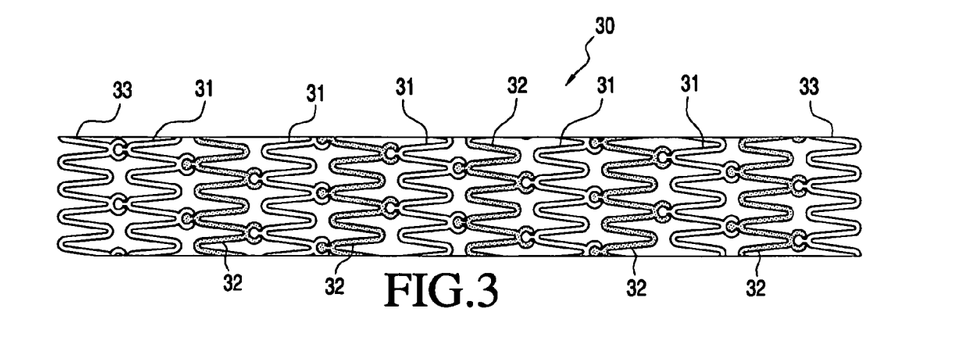
FIG. 3 is a side view of the vascular prosthesis of FIG. 1 wherein alternating segments comprise different materials.

Referring to FIG. 3, in accordance with one aspect of the present invention, inner segments 11 may comprise different materials, strut configurations, or types of radially expandable segments that are selectively intermixed to customize the vascular prosthesis for a specific patient or application. Segments also may include side-branch apertures for use in treating bifurcated vessels, graft covered segments for excluding aneurysms and drug-eluting segments that are pre-loaded with a predetermined amount of drug and may be assembled to provide a desired dose.

For example, whereas metallic radially expandable inner segments provide increased radial stiffness in the deployed configuration, bioabsorbable or drug-eluting radially expandable segments may be better suited for drug delivery. In the embodiment of FIG. 3, vascular prosthesis 30 comprises five metallic segments 31 alternating with five drug-eluting segments 32, all disposed between end segments 33. In a preferred embodiment, the drug may comprise a tetrazole-containing rapamycin for use in treating restenosis, such as described in U.S. Pat. No. 6,015,815 to Mollison, which is incorporated herein by reference in its entirety.

Alternatively, because joints 34 comprise ball elements 35 and socket elements 36 that are common for segments 31, 32 and 33, the segments may be assembled in any order desired for a specific patient or application. Thus, for example, segments 32 and 33 may be reordered so that the five metallic segments are at one end of the stent, and the five polymeric segments are at the other end. Of course, as would be appreciated by those of skill in the art, many other combinations of materials are possible without departing from the scope of the invention.

Figure 4:
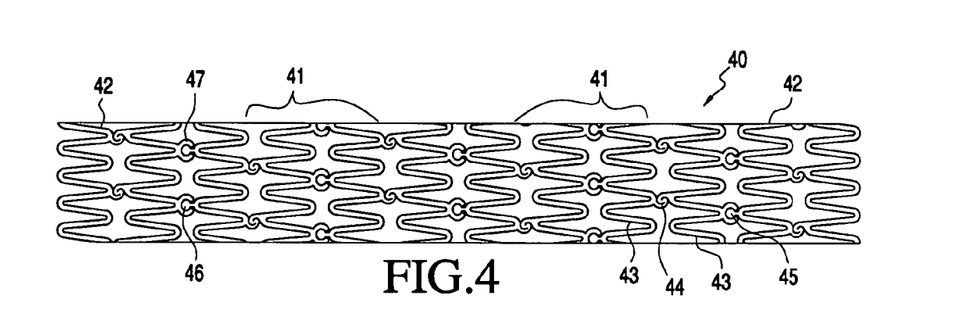
FIG. 4 is a side view of the vascular prosthesis of FIG. 1 wherein each segment includes additional flexible interconnections.

Referring to FIG. 4, in accordance with a further embodiment of the present invention, vascular prosthesis 40 comprises a plurality of inner segments 41 disposed between end segments 42. Each inner segment 41 illustratively comprises two zig-zag hoops 43 coupled by spiral joints 44 to further increase the longitudinal flexibility of the segment. Segments 41 further include joints 45 comprising ball elements 46 and socket elements 47 that enable the segment to be coupled to adjacent segments 41 and end segments 42 to assemble the stent to a desired length. As for the previous embodiments, joints 45 also enhance flexibility of the stent during transluminal insertion.

Figure 5:
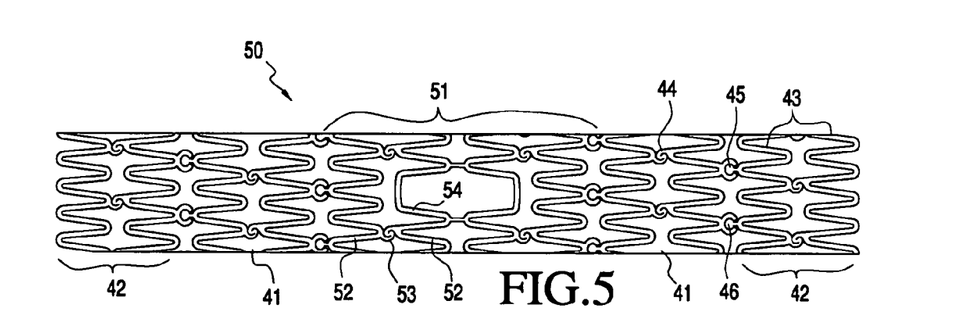
FIG. 5 is a side view of a prosthesis constructed in accordance with the present invention wherein one segment includes a portion defining a side-branch aperture.

Referring to FIG. 5, an alternative embodiment of vascular prosthesis 40 suitable for use in a bifurcated vessel is described. As noted hereinabove, stents having side-branch openings are known in the art, such as described in the aforementioned Von Oepen patent. One of the difficulties of such previously-known stents is that the regions proximal and distal to the side-branch opening are fixed at the time of manufacture and may be unsuitable for a particular patient. For example, the proximal or distal region may partially occlude collateral vessels.

Stent 50 of FIG. 5 solves this foregoing problem by permitting the clinician to tailor the lengths of the proximal and distal regions as desired for a specific patient or application. In particular, stent 50 comprises inner segments 41 and end segments 42 as depicted in FIG. 4, where each segment 41 and 42 further comprises hoops 43 coupled by spiral joints 44 and ball and socket elements 45 and 46, respectively. In addition, stent 50 includes inner segment 51 comprising hoops 52 coupled by spiral joints 53 and defining side-branch aperture 54.

Illustratively, stent 50 includes single segment 41 coupled on either side, however, it is to be understood that any number of segments 41 could be coupled on either side of inner segment 51. In addition, more than one inner segment 51 may be employed, with the side-branch apertures 54 disposed at different circumferential orientations, thereby enabling access to multiple side branch vessels. Accordingly, the vascular prosthesis of the present invention may be assembled by the clinician to match the anatomy of a specific patient's vasculature shortly before implantation and inner segments of various lengths and configurations may be intermixed as necessary to match the patient's vasculature.

Figure 6:
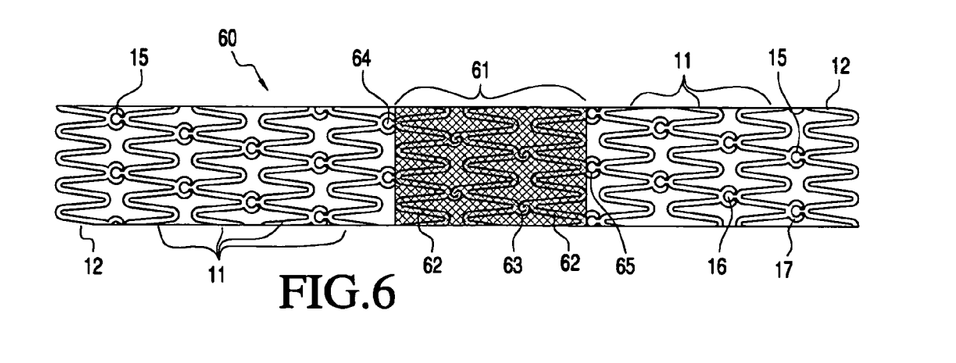
FIG. 6 is a side view of a prosthesis constructed in accordance with the present invention wherein one segment includes a graft covering for use in excluding an aneurysm.

With respect to FIG. 6, a further alternative embodiment of the vascular prosthesis of the present invention is described for use in excluding an aneurysm. Stent 60 is similar in design to the stent of FIG. 1, except that it includes a graft covered segment. More particularly, stent 60 includes a plurality of inner segments 11 interposed between end segments 12. Each of inner segments 11 includes ball and socket elements 16 and 17, respectively, that engage a corresponding element on an adjacent segment to form joints 15.

Stent 60 further comprises inner segment 61, illustratively having a configuration similar to that of segment 41 of FIG. 4. In particular, segment 61 comprises zig-zag hoops 62 coupled by spiral joints 63, with the outermost hoops including ball elements 64 and socket elements 65 that engage the adjacent segments. In accordance with this aspect of the present invention, segment 61 includes graft covering, such as Dacron or expanded polytetrafluoroethylene (ePTFE), affixed to its outer surface by a biocompatible adhesive or sutures. In this manner, stent 60 may be assembled to include one or more segments 61 to exclude an aneurysm within a vessel, yet continue to permit blood flow to reach healthy vessel wall upstream and downstream of the aneurysm.

Figure 7:
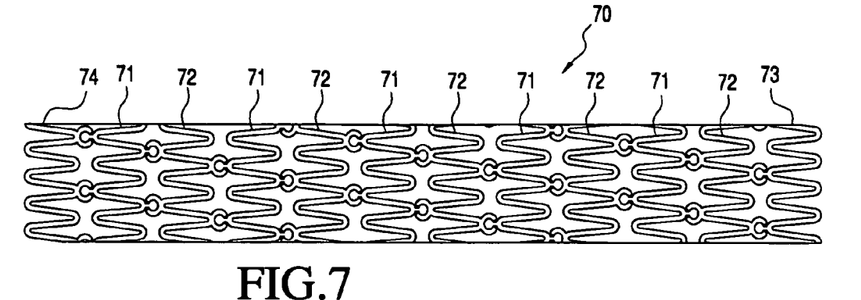
FIG. 7 is a side view of an alternative embodiment of the prosthesis of the present invention wherein alternating modular segments include either all ball elements or all socket elements.

Referring to FIG. 7, a further alternative embodiment of the vascular prosthesis of the present invention is described. Vascular prosthesis 70 comprises inner segments 71, inner segments 72 and end segments 73 and 74. Each segment 71-74 comprises a plurality of struts joined by bends to form zig-zag hoops. Whereas inner segments 11 of the embodiment of FIG. 1 included ball elements at one end and socket elements at the other, segments 71 include only ball elements at either end and segments 72 include only socket elements at either end. End segment 73 includes only ball elements at one end and end segment 74 includes only socket elements at one end. As will be understood, segments 71 and 72 may include the same or different strut configurations, may be of the same or different lengths or may have the same or different mechanical properties.

Figure 8:
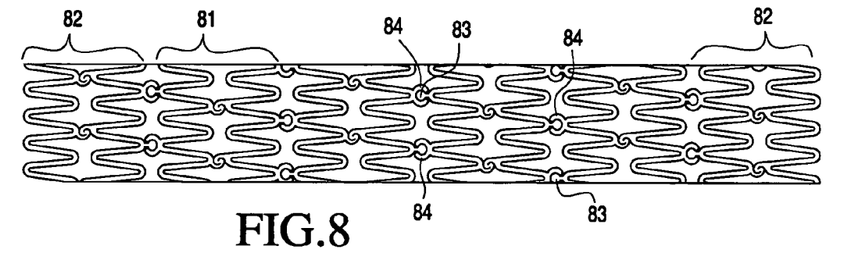
FIG. 8 is a side view of an alternative embodiment of the prosthesis of the present invention wherein each segment that combines both ball and socket elements at each end.

Referring now to FIG. 8, a still further alternative embodiment of the vascular prosthesis of the present invention is described. Vascular prosthesis 80 is similar in construction to stent 40 of FIG. 4, and comprises inner segments 81 and end segments 82. Unlike inner segments 41, which included only ball elements at one end and socket elements at the other, segments 81 have ball elements 83 alternating with socket elements 84 around the circumference of the segment at either end.

As for the previous embodiments, segments 81 may have the same or different strut configuration, the same or different lengths or the same or different mechanical properties.

Figure 9A:
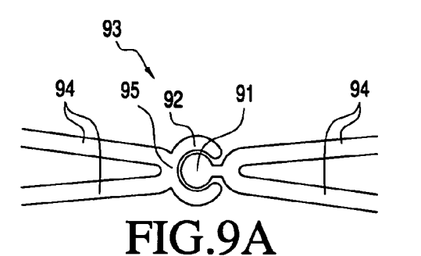
FIGS. 9A and 9B are, respectively, side views of a locking ball and socket joint of the present invention depicted in the delivery configuration and the deployed configuration.
Figure 9B:
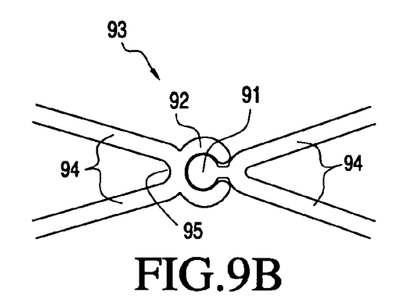

With respect to FIGS. 9A and 9B, in accordance with a further aspect of the invention, locking joints suitable for use in the vascular prostheses of FIGS. 1-8 are described. Ball elements 91 and socket elements 92 of FIG. 9 are designed to add structural rigidity to joints 93 of a vascular prosthesis in the deployed configuration. In particular, as zig-zag segments 94 expand from the delivery configuration (FIG. 9A) to the expanded deployed configuration (FIG. 9B), socket element 92 functions as pliers that partially closes around ball element 91, thereby fixedly engaging the ball element and enhancing the structural rigidity of the assembled prosthesis.

To facilitate this pliers-like action of socket elements 92, bends 95 preferably comprise reduced thickness regions, thereby facilitating expansion of the segments into the deployed configuration. Providing thinner bends 95 also promotes closing of socket element 92 around ball element 91 as the arms of the socket element are forced together during expansion of the vascular prosthesis, as depicted in FIG. 9B. Advantageously, the closing action of socket element 92 about ball element 91 reduced the risk of disengagement of adjacent segments of vascular prosthesis in the deployed configuration.

Figure 10:
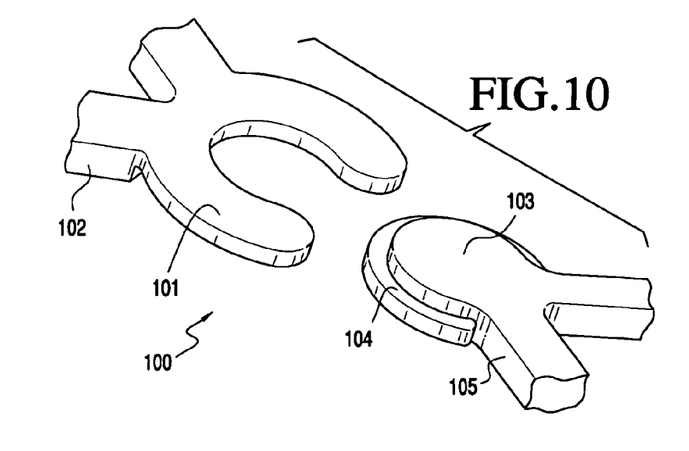
FIG. 10 is a perspective view of further alternative ball and socket joint that permits self-expanding segments and balloon-expandable segments to be intermixed.

With respect to FIG. 10, a further embodiment of a ball and socket joint suitable for use with vascular prosthesis of the present invention is described. In the preceding embodiments the socket elements generally are of uniform thickness. In FIG. 10, however, joint 100 comprises socket element 101 has a thickness equal to about half of strut thickness 102 and ball element 103 including flange 104, wherein the flange also has a thickness of about one-half strut thickness 105. When coupled together, ball element 103 projects into socket element 101, while flange 104 bears against the underside of socket element 101. In this manner, ball element 103 is free to articulate within socket element 101, but flange 104 prevents ball element 103 from passing entirely through the socket element.

Joint embodiment of FIG. 10 may be particularly advantageous when used in conjunction with the stent of FIG. 7, especially where the inner segments 71 and 72 are selected to have different radial expansion properties, e.g., such as resilient self-expanding segments and rigid balloon-expandable segments. If segments 72 (which have all socket elements) are made of a rigid balloon-expandable material and segments 71 (which have all ball elements) are made of a resilient self-expanding material, joints 100 may be used to facilitate crimping the assembled stent onto a balloon catheter. In particular, because ball elements 103 are captured by flange 104 within socket 101, the self-expanding segments will be compressed onto the balloon when the rigid segments are crimped onto the balloon.

In addition, because joints 101 may be configured to provide the locking feature described with respect to the embodiment of FIG. 9, joints 100 also may be used to lock the segments of the stent together in the deployed configuration, thereby preventing disengagement of adjacent segments.

Figure 11:
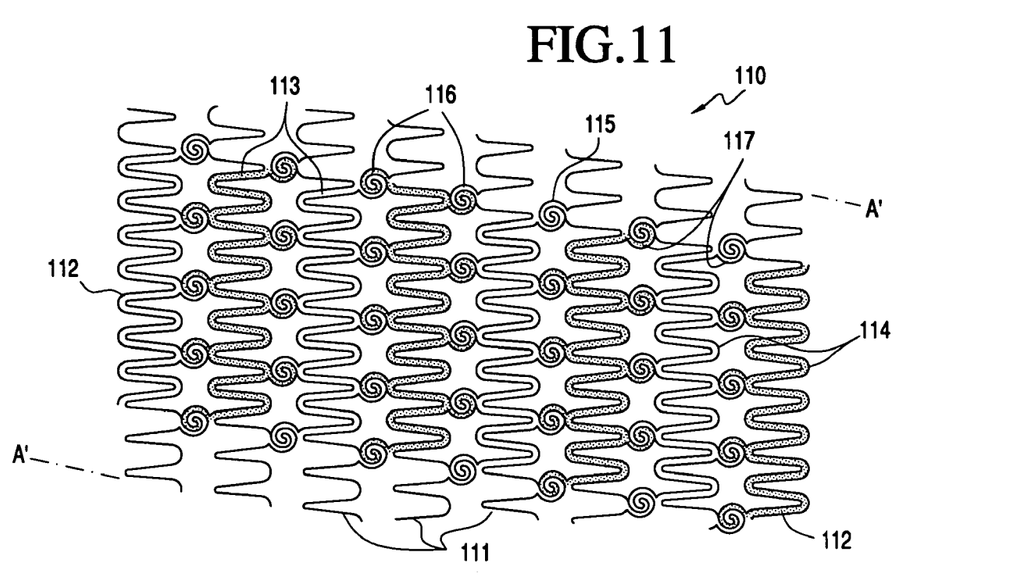
FIG. 11 is a plan view of an embodiment of a modular vascular prosthesis of the present invention that has been cut along line A-A and flattened in which the interconnected joints comprise intertwined spiral elements.

Referring now to FIG. 11, a second family of embodiments of a vascular prosthesis constructed in accordance with the principles of the present invention is described. Vascular prosthesis 110, for example, a stent, is shown cut along line A'-A' along its longitudinal axis and flattened into a plane for illustrative purposes. As in the first family of embodiments, vascular prosthesis 110 comprises a tube-like structure made up of a plurality of interconnected modular segments, including inner segments 111 and end segments 112.

Segments 111 and 112 comprise a plurality of struts 113 joined at the ends by bends 114 to form a generally zig-zag configuration in the deployed configuration. As would be understood by one of ordinary skill in the art, segments 111 and 112 may comprise many alternative strut configurations without departing from the scope of the present invention.

Figure 13:
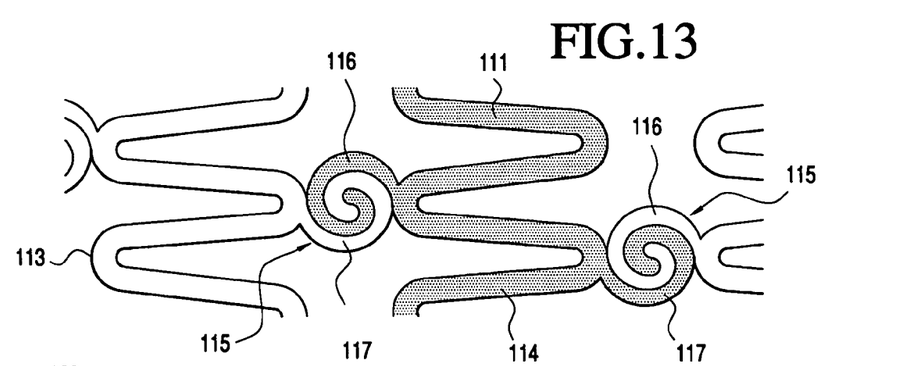
FIG. 13 is a detailed view of the intertwined spiral elements of the embodiment of FIG. 11.

Referring now also to the enlarged depiction of FIG. 13, joints 115 interconnect segments 111 and 112. Each joint 115 comprises intertwined spiral elements 116 and 117, wherein elements 116 and 117 have a common orientation, either clockwise or counterclockwise, that enables the elements to intertwine. Inner segments 111 include spiral elements 116 and 117 at either end, while end segments 112 include such elements on only one end. Spiral elements 116 and 117 preferably are formed as extensions on selected bends 114 disposed between struts 113 around the circumference of the stent. Illustratively, alternating segments in FIGS. 11 and 13 are shaded for purposes of delineating the shapes of spiral elements 116 and 117, and the segments may comprise the same or different materials.

In FIGS. 11 and 13, spiral elements 116 are disposed on one end of each inner segment 111 and open downwards, whereas spiral elements 117 are disposed on the other end of the segment and open upwards. As will be apparent from inspection, the relative positions of spiral elements 116 and 117 may be interchanged by flipping the segment 180 degrees relative to the longitudinal axis of the prosthesis. Adjacent spiral elements are depicted as having one intervening bend 114 around the circumference of the stent, but may include two or more intervening bends. Joints 115 permit a significant degree of articulation between adjacent segments, particularly in the delivery configuration, making the stent highly flexible and thus able to negotiate tortuous anatomy.

As noted with respect to the embodiments of FIGS. 1-10, the zig-zag configuration of struts 113 and bends 114 depicted in FIG. 11 preferably is formed by laser cutting a solid tube. Vascular prosthesis 110 preferably is flexible enough to conform to the shape of a delicate vessel without substantially remodeling the vessel. In particular, the zig-zag configuration of segments 111 and 112 is expected to conform to a natural curvature of a vessel wall. Of course, other patterns of struts and bends, such as are known in the art, advantageously be used within segments 111 and 112.

Figure 12A:
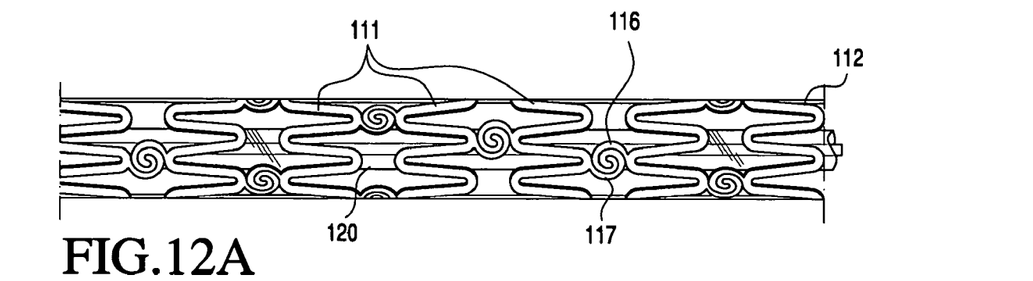
FIGS. 12A and 12B are, respectively, perspective views of the modular vascular prosthesis of FIG. 11 disposed in the delivery configuration around a balloon catheter and in the deployed configuration.

Referring to FIG. 12A, vascular prosthesis 110 comprises a balloon expandable material and is shown crimped in a contracted delivery configuration over balloon 120 of a balloon catheter. This may be accomplished by assembling a desired number of inner segments 111 between end segments 112 to provide a stent of a desired length, and the assembled stent may then be crimped onto balloon 120 using any of a number of previously-known crimping devices. Because the stent is retained centered on balloon 120, spiral elements 116 and 117 remain in engagement to form a substantially smooth exterior surface of the stent.

Figure 12B:
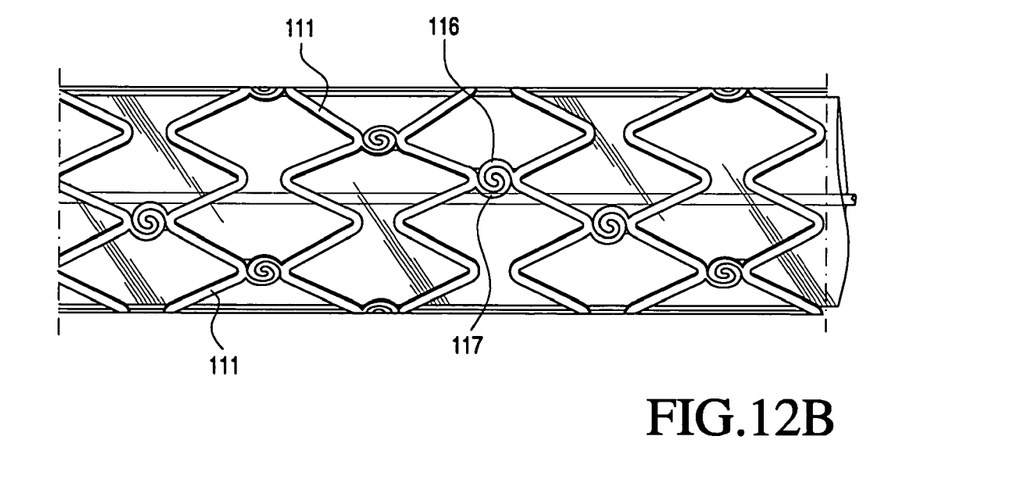

The balloon catheter carrying the stent of FIG. 12 may be delivered transluminally to a target site within a patient's vessel using well-known techniques. Joints 115 permit vascular prosthesis 110 to flex along its length to negotiate tortuous anatomy. Vascular prosthesis 110 or portions of the catheter may be radiopaque to facilitate positioning within the vessel. The target site may, for example, comprise a stenosed region of the vessel at which an angioplasty procedure has been conducted.

Referring to FIG. 12B, balloon 120 is inflated to expand vascular prosthesis 110 to the deployed configuration in which it engages and supports the wall of the vessel at the target site. As shown in FIG. 12B, spiral elements 116 continue to be retained in spiral elements 117 when segments 111 and 112 are radially expanded. Balloon 120 is then deflated and the balloon catheter is removed from the vessel, leaving vascular prosthesis 110 supporting the vessel. The web structure of vascular prosthesis 110 provides sufficient radial stiffness to maintain vascular prosthesis 110 in the expanded configuration, with minimal recoil. Vascular prosthesis 10 optionally may comprise an external coating configured to inhibit restenosis.

As for the embodiments of FIGS. 1-10, inner segments 111 of the embodiments of FIGS. 11-13 may comprise different materials, strut configurations, or types of radially expandable segments that are selectively intermixed to customize the vascular prosthesis for a specific patient or application. Segments also may include side-branch apertures for use in treating bifurcated vessels, graft covered segments for excluding aneurysms and drug-eluting segments that are pre-loaded with a predetermined amount of drug and may be assembled to provide a desired dose, such as described hereabove.

For example, whereas metallic radially expandable inner segments provide increased radial stiffness in the deployed configuration, bioabsorbable or drug-eluting radially expandable segments may be better suited for drug delivery. Vascular prosthesis 110 therefore may comprise four metallic segments alternating with four drug-eluting segments, illustratively corresponding to the shaded and unshaded segments in FIG. 11.

Because joints 115 are common for all segments of the prosthesis 110, the segments may be assembled in any order desired for a specific patient or application. Thus, for example, the segments may be reordered so that the four metallic segments are at one end of the stent, and the four polymeric segments are at the other end. Of course, as would be appreciated by those of skill in the art, many other combinations of materials are possible without departing from the scope of the invention.

Figure 14A:
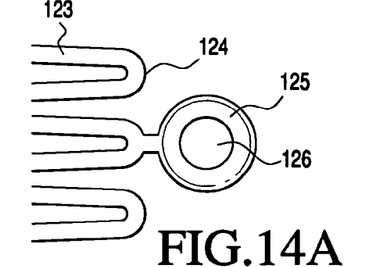
FIG. 14A-14C are, respectively, views of a marker opening and radio-opaque rivet as may be applied on the end loops of the prostheses depicted in FIGS. 1 and 11.
Figure 14B:
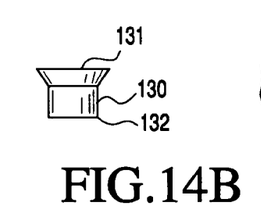
Figure 14C:
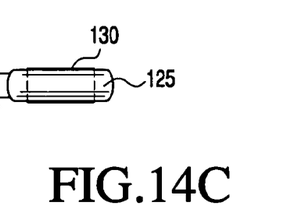

Referring now to FIGS. 14A to 14C, a first approach to providing a radio-opaque marker on any of the prostheses of FIGS. 1-12 is described. In FIG. 14A, struts 123 (corresponding to struts 13 of FIG. 1 or struts 113 of FIG. 11) are connected by bends 124 (corresponding to bends 14 of FIG. 1 or bends 114 of FIG. 11). In accordance with this aspect of the present invention, selected bends 124 on either or both end segments (segment 12 in FIG. 1; segment 112 in FIG. 11) include marker housings 125, in which a radiopaque marker may be disposed. Preferably, marker housings 125 are designed such that the mechanical properties of the bend of the prosthesis are not affected. Alternatively, marker housings 125 may be configured such that the marker housings function as a structural member of the prosthesis.

As shown in FIG. 14A, marker housing 125 includes aperture 126 formed therein, wherein the aperture has a generally circular shape. As will be understood, aperture 126 may be formed having other shapes, such as rectangular, square, oval, octagonal, and the like. A radio-opaque marker may be disposed within aperture 126 of marker housing 125, and may comprise any material having greater radio-opacity than the material from which the prosthesis is constructed. Examples of suitable material include, stainless steel, gold, silver, cobalt, platinum, iridium, tantalum, and alloys thereof or similar biocompatible or bioabsorbable materials. In a preferred embodiment, the marker comprises tantalum.

As shown in FIG. 14B, the marker may be embodied in the form of rivet 130 having a generally cylindrical shape and first end 131 and second end 132. Rivet 130 may be manufactured as a composite, wherein one material may be radiopaque and the other material may be a therapeutic agent, e.g., a drug that elutes from the marker after implantation. In this case, rivet 130 may comprise a biocompatible material, such as described above.

Still referring to FIG. 14B, first end 131 of rivet 130 may have an enlarged diameter configured to retain the rivet within aperture 126 of marker housing 125 prior to deformation of second end 132 of the rivet. FIG. 14C depicts marker housing 125 in which rivet 130 has been disposed and second end 132 of the rivet has been deformed to lock the rivet into engagement with the marker housing.

Rivet 130 alternatively may be constructed of multiple pieces that may then be assembled to form a single member when disposed within a marker housing in accordance with the present invention. For example, the rivet may comprise upper, middle, and lower pieces, wherein the middle piece includes means to affix the upper and lower pieces thereto, such as a protrusion extending from each end of the middle piece, wherein the upper and lower pieces include an aperture or recessed area configured to receive the protrusion. Alternatively, a fourth piece may be utilized to affix the upper, middle and lower pieces together to form a marker in accordance with the present invention.

The rivet may be manufactured from a sheet of material, wherein the rivets are produced by stamping and a second process is performed to form the enlarged diameter section. Alternatively, the rivets may be manufactured by cutting the rivets from round stock, wherein the cut portions may then be tumbled to radius the edges then machined to produce the increased radius portion. Further still, the rivets may be manufactured utilizing other known techniques such as injection molding, casting, machining, hydroforming and the like.

Alternatively, the marker may be integrally formed with the prosthesis device during manufacturing. Such a process would involve manipulating a tubular member or a sheet of material from which the prosthesis is constructed prior to the formation of the prosthesis. For example, if the prosthesis were to be formed from a thin-walled tubular member, a groove or other feature may be formed in one of the walls of the tube, and a radio-opaque material then disposed within the groove or feature. Alternatively, the locations of the marker housing may be pre-formed on the device and the markers may be pre-disposed within the marker housings prior to the manufacture of the prosthesis device, which may then be constructed according to known methods.

Figure 15:
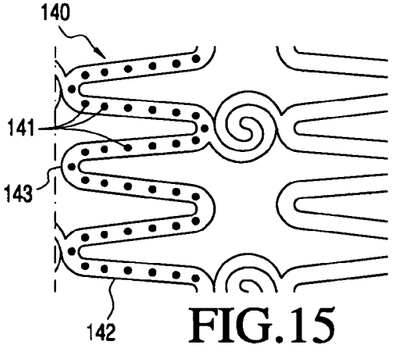
FIG. 15 is an alternative arrangement for providing radio-opaque markers on the prosthesis of the present invention.

Referring to FIG. 15, an alternative approach to providing radio-opaque markers on the prosthesis of the present invention is described. Prosthesis 140, illustratively of the type described with respect to FIG. 11, includes a plurality of markers 141 disposed along at least one of struts 142 and bends 143. Markers 141 may be comprised of rivets disposed within openings formed in the strut members as described above or alternatively, the markers may be integrally formed upon the strut member during fabrication of the prosthesis.

For example, the prosthesis may be formed from a tubular member, wherein the struts and bends are formed in the tubular member utilizing laser cutting or similar processes. Markers 141 may be formed on the struts 142 and bends 143 by cutting away, machining away, chemical milling, or electropolishing material away from the struts to form markers 141. Although markers 141 are illustratively depicted as round in FIG. 15, the markers may be formed having any shape or profile.

Figure 16:
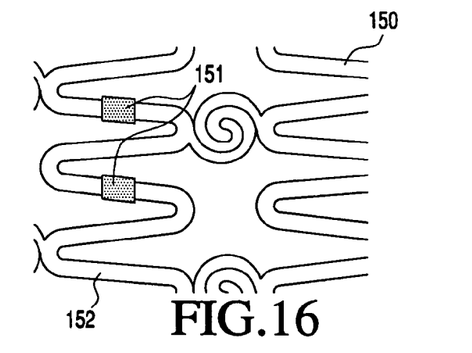
FIG. 16 is another alternative arrangement for providing radio-opaque markers on the prosthesis of the present invention.

In FIG. 16, a further alternative approach to providing radio-opaque markers on the prosthesis of the present invention is described. Prosthesis 150, illustratively of the type described with respect to FIG. 11, includes a plurality of markers 151 disposed along at least one of struts 152. Markers 151 comprise a clip or a band that may be attached to struts 152, and may be constructed of a material such as tantalum, gold, gold plating, silver, silver plating, alloyed metals, polymers, plastics, or similar biocompatible or bioabsorbable materials. Markers 152 may be configured to be retained on the prosthesis by deforming the marker such that the marker is frictionally retained on the prosthesis. Alternatively, markers 152 may be affixed to the prosthesis utilizing other methods such as welding, gluing, swaging, or similar methods.

It is contemplated that the markers described above may be formed anywhere along the length of the prosthesis. For example, it is contemplated that marker housings or markers may be formed for example in the middle of the prosthesis to indicate a specific area or property of the prosthesis. As such, markers may be disposed in marker housings formed within the struts or bends of the prosthesis, or integrated in the prosthesis anywhere along the length of the prosthesis. Further still, a variety of the marker embodiments described and shown herein may be utilized in any combination along the length of an prosthesis according to the present invention, wherein different marker embodiments may be utilized to mark locations of interest.

Figure 17:
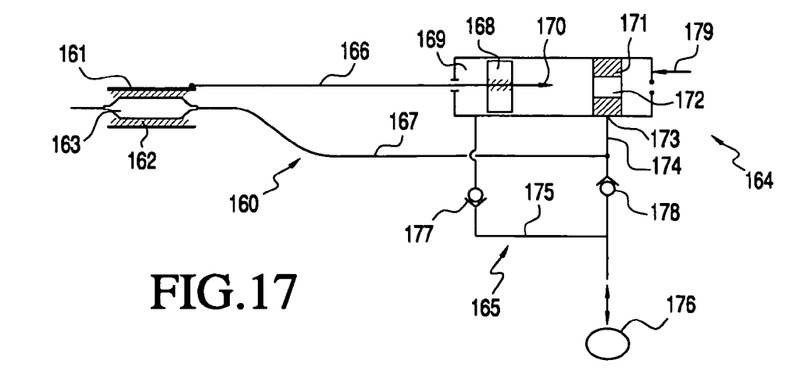
FIG. 17 is an illustrative delivery system for use in delivering the prosthesis of the present invention.

Referring now to FIG. 17, an illustrative delivery system for use with the prostheses of the present invention is described, such as described in greater detail in International Publication No. WO 2004/014256. That publication is incorporated herein by reference in its entirety. More particularly, delivery system 160 includes sheath 161 is arranged on stent 162 supported by balloon 163. Sheath 161, stent 162 and balloon 163 are supported by a catheter (not shown), which may be inserted into a patient's vasculature. Sheath retraction device 164 and fluid pressure 165 are connected with the delivery system 160 by wire 166 and tube 167, respectively.

Wire 164 connects sheath 161 with piston 168 in cylinder 169. Hook 170 is disposed from the proximal side of piston 168. Cylinder 169 further comprises floating second piston 171 with opening 172 that can be penetrated by hook 170. Floating piston 171 closes outlet 173 in cylinder 169. Tube 167 connects balloon 163 with tube 174 mounted at outlet 173 of cylinder 169. Tube 175 is connected to a inflation/deflation device schematically shown as double-arrow 176 at the one end and via a unidirectional valve (check valve) 177 with cylinder 169 at the other end. Furthermore, tube 175 is connected via a unidirectional valve (check valve) 178 with tube 167.

Operation of delivery system 160 is as follows: Balloon 163 is in a deflated state and sheath 161 covers stent 162. Floating second piston 171 is positioned so that outlet 173 of cylinder 169 and, thus tube 174, are closed. A clinician applies pressure from inflation/deflation device 176 to tube 175. The pressure shuts unidirectional valve 178 and opens unidirectional valve 177. This causes pressurized fluid to flow into cylinder 169 and shifts first piston 168 in the proximal direction, thereby retracting wire 166 and sheath 161 from stent 162. The delivery system is designed so that the pressure required to move piston 168 is very low.

When first piston 168 reaches floating second piston 171, the proximal end of wire 166 with hook 170 penetrates opening 172 in piston 171, and piston 168 moves piston 171 to the proximal end of cylinder 169. Hook 170 engages hook holder 179, wherein piston 168 with wire 166 and sheath 161 is fixed at the proximal end. In this position, sheath 161 is completely retracted from stent 162, and outlet 173 of cylinder 1169 is open. In this manner, the pressurized fluid from the inflation/deflation device 176 flows via tube 175 and the left side of cylinder 169 through outlet 173, tube 174 and tube 167 to balloon 163, and inflates the balloon to deploy stent 162. The pressure may be applied until a desired expanded diameter is attained for the prosthesis.

Once the prosthesis is deployed, the clinician applies a vacuum from the inflation/deflation device 176 via unidirectional valve 178 and tube 166 to balloon 163. During this suction step, unidirectional valve 177 is closed. At the end of the stent delivery and deployment process, the catheter with balloon 163 and sheath 161 is removed from the patient's vessel, leaving the prosthesis in the desired position within the vessel.

It is to be understood that the foregoing delivery system is merely illustrative of the types of delivery systems that may be used to deliver and deploy the prostheses of the present invention.

Alternatively, a delivery system such as described in co-pending, commonly assigned U.S. patent application Ser. No. 10/932,964, filed Sep. 2, 2004, and entitled "Delivery System For A Medical Device," which is incorporated herein by reference, may be employed It should be understood that any of the foregoing joint configurations and specialized modular segments may be interchangeably used with any of the vascular prostheses of the preceding embodiments. In this manner, the methods and apparatus of the present invention permit a vascular prosthesis to be tailored to a given patients anatomy or a specific application. Although preferred illustrative embodiments of the present invention are described hereinabove, it will be evident to one skilled in the art that various changes and modifications may be made therein without departing from the invention. It is intended in the appended claims to cover all such changes and modifications that fall within the true spirit and scope of the invention

What is claimed is:

1. A modular vascular prosthesis having a delivery configuration and a deployed configuration, the vascular prosthesis comprising:
   a radially expandable first segment having proximal and distal ends, the radially expandable first segment comprising a plurality of first struts coupled by a plurality of first bends, the plurality of first struts and the plurality of first bends having a first thickness;
   a radially expandable second segment having proximal and distal ends, the radially expandable second segment comprising a plurality of second struts coupled by a plurality of second bends, the plurality of second struts and the plurality of second bends having a second thickness;
   a plurality of first inter-engageable elements extending from the distal end of the first segment, the first inter-engageable elements comprising disk shaped portions having a distally extending circumferentially projecting peripheral flange extending from one first strut of the plurality of first struts about a periphery of the disk shaped portion to a second strut of the plurality of first struts, the disk shaped portions having a thickness approximately equal to the first thickness and the circumferentially projecting flange having a thickness that is less than the first thickness; and
   a plurality of second inter-engageable elements extending from the proximal end of the second segment, each of the second inter-engageable elements comprising a socket element directly coupled to a pair of second struts of the plurality of second struts and configured to accept the disk shaped portions and overlie the flange of the first inter-engageable element, the socket element having a thickness that is less than the second thickness,
   wherein the plurality of first inter-engageable elements are engaged in the plurality of second inter-engageable elements to permit articulation of the first segment relative to the second segment in the delivery configuration.

2. The modular vascular prosthesis of claim 1 wherein the pluralities of first and second inter-engageable elements fixedly engage each other in the deployed configuration while forming a substantially uniform transition between said radially expandable first segment and said radially expandable second segment.

3. The modular vascular prosthesis of claim 1, wherein the first and second segments comprise hoops having a generally zig-zag configuration.

4. The modular vascular prosthesis of claim 3 wherein at least one of the first and second segments comprises first and second hoops having a generally zig-zag configuration.

5. The modular vascular prosthesis of claim 4 wherein the first and second hoops are coupled by flexible spiral joints.

6. The modular vascular prosthesis of claim 1, wherein first segment has a first length and the second segment has a second length, and the first and second lengths are different.

7. The modular vascular prosthesis of claim 1, wherein first segment comprises a first material and the second segment comprises a second material, and the first material is different than the second material.

8. The modular vascular prosthesis of claim 7, wherein the first material comprises a metal alloy and the second material comprises a polymer.

9. The modular vascular prosthesis of claim 1, wherein first segment possesses a first set of mechanical properties and the second segment possesses a second set of mechanical properties, and the first set of mechanical properties is different than the second set of mechanical properties.

10. The modular prosthesis of claim 9 wherein the first segment is balloon expandable and the second segment is self-expanding.

11. The modular vascular prosthesis of claim 1, wherein first segment has a first strut configuration and the second segment has a second strut configuration, and the first strut configuration is different than the second strut configuration.

12. The modular vascular prosthesis of claim 1, wherein at least one of the first and second segments comprises a drug-eluting polymeric material.

13. The modular vascular prosthesis of claim 1, wherein at least one of the first and second segments includes a side-branch aperture.

14. The modular vascular prosthesis of claim 1, wherein at least one of the first and second segments includes a cover comprising a biocompatible graft material.

15. The modular vascular prosthesis of claim 1, further comprising:
   a plurality of second inter-engageable elements extending from the distal end of the second segment.

16. The modular vascular prosthesis of claim 1, further comprising:
   a plurality of first inter-engageable elements extending from the proximal end of the first segment; and
   a plurality of second inter-engageable elements extending from the distal end of the second segment.

17. The modular vascular prosthesis of claim 1, further comprising:
   a plurality of second inter-engageable elements extending from the distal end of the first segment, individual ones of the plurality of second inter-engageable elements interleaved with individual ones of the first inter-engageable elements extending from the distal end of the first segment; and
   a plurality of first inter-engageable elements extending from the proximal end of the second segment, individual ones of the plurality of first inter-engageable elements interleaved with individual ones of the second inter-engageable elements extending from the proximal end of the second segment.

18. A modular vascular prosthesis having a delivery configuration and a deployed configuration, the modular vascular prosthesis having a longitudinal axis, the vascular prosthesis comprising:
- a radially expandable first segment having proximal and distal ends;
- a radially expandable second segment having proximal and distal ends;
- a plurality of first inter-engageable elements extending from the distal end of the first segment; and
- a plurality of second inter-engageable elements extending from the proximal end of the second segment,
- wherein the plurality of first inter-engageable elements are engaged in the plurality of second inter-engageable elements to permit articulation of the first segment relative to the second segment in the delivery configuration, and
- wherein each of the pluralities of first and second inter-engageable elements comprise spiral elements forming independent, distinct structures configured to selectively intertwine with one another in an arrangement of complementary intertwining spirals while in both the delivery configuration and the deployed configuration to form a substantially uniform transition between said radially expandable first segment and said radially expandable second segment and a substantially smooth exterior surface to the modular vascular prosthesis, and to selectively couple the first segment and the second segment.

19. A modular vascular prosthesis having a delivery configuration and a deployed configuration, the vascular prosthesis comprising:
- a plurality of radially expandable first segments having proximal and distal ends, the plurality of radially expandable first segments having a first thickness;
- a plurality of radially expandable second segments having proximal and distal ends, the plurality of radially expandable second segments having a second thickness;
- a plurality of first inter-engageable elements extending from the distal ends of the first segments, the first inter-engageable elements comprising disk-shaped portions having a circumferentially projecting peripheral flange extending from a first strut of a pair of struts about a periphery of the disk shaped portion to a second strut of the pair of struts, the disk-shaped portions having a thickness approximately equal to the first thickness and the circumferentially projecting flange having a thickness that is less than the first thickness; and
- a plurality of second inter-engageable elements extending from the proximal ends of the second segments, the plurality of second inter-engageable elements engaged with the plurality of first inter-engageable elements, each of the second inter-engageable elements being connected to two struts of the second plurality of struts and comprising a socket configured to accept the disk-shaped portion and overlie the flange, the socket having a thickness that is less than the second thickness,
- wherein the first segments possess a first set of mechanical properties and the second segments possess a second set of mechanical properties, and the first set of mechanical properties is different than the second set of mechanical properties, and
- wherein the plurality of first inter-engageable elements and the plurality of second inter-engageable elements engage to form a plurality of connections that have a thickness that is substantially equal to the first and second thicknesses while forming a substantially uniform transition between said radially expandable first segment and said radially expandable second segment.

20. The modular vascular prosthesis of claim 19 wherein the pluralities of first and second inter-engageable elements fixedly engage each other in the deployed configuration.

21. The modular vascular prosthesis of claim 19, wherein first segments comprise a first material and the second segments comprise a second material, and the first material is different than the second material.

22. The modular vascular prosthesis of claim 21, wherein the first material comprises a metal alloy and the second material comprises a polymer.

23. The modular vascular prosthesis of claim 19, wherein first segments have a first strut configuration and the second segments have a second strut configuration, and the first strut configuration is different than the second strut configuration.

24. The modular vascular prosthesis of claim 19, wherein the first segments have a first length and the second segments have a second length, and the first and second lengths are different.

25. The modular vascular prosthesis of claim 19, wherein at least a subset of plurality of first segments comprises a drug-eluting polymeric material.

26. The modular vascular prosthesis of claim 19, wherein at least one of the plurality of first segments includes a side-branch aperture.

27. The modular vascular prosthesis of claim 19, wherein at least one of the plurality of first segments includes a cover comprising a biocompatible graft material.

28. The modular vascular prosthesis of claim 19, further comprising:
- a plurality of second inter-engageable elements extending from the proximal ends of the first segments; and
- a plurality of first inter-engageable elements extending from the distal ends of the second segments.

29. The modular vascular prosthesis of claim 19, further comprising:
- a plurality of first inter-engageable elements extending from the proximal ends of the first segments; and
- a plurality of second inter-engageable elements extending from the distal ends of the second segments.

30. A modular vascular prosthesis having a delivery configuration and a deployed configuration, the vascular prosthesis comprising:
- a plurality of radially expandable first segments having proximal and distal ends;
- a plurality of radially expandable second segments having proximal and distal ends;
- a plurality of first inter-engageable elements extending from the distal ends of the first segments; and
- a plurality of second inter-engageable elements extending from the proximal ends of the second segments, the plurality of second inter-engageable elements engaged with the plurality of first inter-engageable elements, and
- wherein each of the pluralities of first and second inter-engageable elements comprise spiral elements forming independent, distinct structures configured to selectively intertwine with one another in an arrangement of complementary intertwining spirals while in both the delivery configuration and the deployed configuration to form a substantially uniform transition between said radially expandable first segment and said radially expandable second segment, a substantially smooth exterior surface to the modular vascular prosthesis, and to selectively couple the first segment and the second segment.

* * * * *